US010258492B2

(12) United States Patent
Majercak et al.

(10) Patent No.: US 10,258,492 B2
(45) Date of Patent: Apr. 16, 2019

(54) PROSTHESIS DELIVERY SYSTEM WITH AXIALLY COLLAPSIBLE SHEATH

(71) Applicant: Cook Medical Technologies LLC, Bloomington, IN (US)

(72) Inventors: David C. Majercak, Bloomington, IN (US); Mark R. Frye, Bloomington, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 49 days.

(21) Appl. No.: 15/449,007

(22) Filed: Mar. 3, 2017

(65) Prior Publication Data

US 2018/0250150 A1 Sep. 6, 2018

(51) Int. Cl.
| | |
|---|---|
| *A61F 2/95* | (2013.01) |
| *A61F 2/966* | (2013.01) |
| *A61B 17/34* | (2006.01) |
| *A61F 2/00* | (2006.01) |
| *A61F 2/01* | (2006.01) |

(Continued)

(52) U.S. Cl.
CPC .......... *A61F 2/966* (2013.01); *A61B 17/3468* (2013.01); *A61B 17/12122* (2013.01); *A61B 2017/12054* (2013.01); *A61F 2/0063* (2013.01); *A61F 2/01* (2013.01); *A61F 2/07* (2013.01); *A61F 2/2475* (2013.01); *A61F 2/82* (2013.01); *A61F 2002/0072* (2013.01); *A61F 2002/011* (2013.01); *A61F 2002/9517* (2013.01);

(Continued)

(58) Field of Classification Search
CPC .... A61F 2/966; A61F 2/97; A61F 2002/9665; A61F 2/962; A61F 2002/9517; A61B 17/3468
See application file for complete search history.

(56) References Cited

U.S. PATENT DOCUMENTS

| | | | |
|---|---|---|---|
| 5,234,411 A | 8/1993 | Vaillancourt | |
| 5,534,007 A * | 7/1996 | St. Germain | ............. A61F 2/95 606/191 |

(Continued)

FOREIGN PATENT DOCUMENTS

| | | |
|---|---|---|
| WO | WO2006/133959 | 12/2006 |
| WO | WO 2016/034171 A2 | 3/2016 |

OTHER PUBLICATIONS

Extended European Search Report for 18275029.9 dated Jun. 27, 2018, 7 pgs.

*Primary Examiner* — Katrina M Stransky
(74) *Attorney, Agent, or Firm* — Brinks Gilson & Lione

(57) ABSTRACT

A prosthesis delivery system and method of use thereof are described. The system includes a handle, an inner cannula extending proximally from the handle, an outer sheath extending proximally from the handle, and a pull member. The outer sheath including an axially collapsible segment and a non-collapsible body. The pull member is coupled between the handle and the axially collapsible segment or the non-collapsible body of the outer sheath. The handle is operable to retract the pull member such that the axially collapsible segment is shortened. The handle may include a spool and an actuator coupled to the pull member in a manner for winding the pull member around the spool. The handle may be shorter than the retraction length of the axially collapsible segment sized for deployment of the prosthesis.

19 Claims, 8 Drawing Sheets

(51) Int. Cl.
  *A61F 2/07* (2013.01)
  *A61F 2/24* (2006.01)
  *A61F 2/82* (2013.01)
  *A61B 17/12* (2006.01)

(52) U.S. Cl.
  CPC ............... *A61F 2250/0018* (2013.01); *A61F 2250/0036* (2013.01)

(56) References Cited

U.S. PATENT DOCUMENTS

| | | |
|---|---|---|
| 6,663,665 B2 | 12/2003 | Shaolian et al. |
| 8,025,691 B2 | 9/2011 | Carter et al. |
| 8,668,668 B2 | 3/2014 | Bishop et al. |
| 8,858,613 B2 | 10/2014 | Cragg et al. |
| 9,211,206 B2 | 12/2015 | Pryor |
| 9,364,357 B2 | 6/2016 | Costello |
| 2001/0044595 A1 | 11/2001 | Reydel et al. |
| 2005/0055077 A1 | 3/2005 | Marco et al. |
| 2005/0245892 A1 | 11/2005 | Elkins et al. |
| 2006/0015171 A1 | 1/2006 | Armstrong |
| 2006/0025844 A1 | 2/2006 | Majercak et al. |
| 2006/0190071 A1 | 8/2006 | Armstrong et al. |
| 2007/0198077 A1 | 8/2007 | Cully et al. |
| 2008/0033396 A1 | 2/2008 | Danek et al. |
| 2008/0132879 A1 | 6/2008 | Rasmussen et al. |
| 2009/0182411 A1 | 7/2009 | Irwin et al. |
| 2010/0049168 A1 | 2/2010 | Parker et al. |
| 2011/0288558 A1* | 11/2011 | Nimgaard ............ A61F 2/95 606/108 |
| 2013/0204345 A1 | 8/2013 | Cully et al. |
| 2014/0188211 A1* | 7/2014 | Roeder ............ A61F 2/966 623/1.12 |
| 2016/0074189 A1 | 3/2016 | Cummins |
| 2016/0074194 A1 | 3/2016 | Cummins et al. |
| 2016/0158050 A1 | 6/2016 | Skelton et al. |
| 2016/0184117 A1 | 6/2016 | Vad et al. |

* cited by examiner

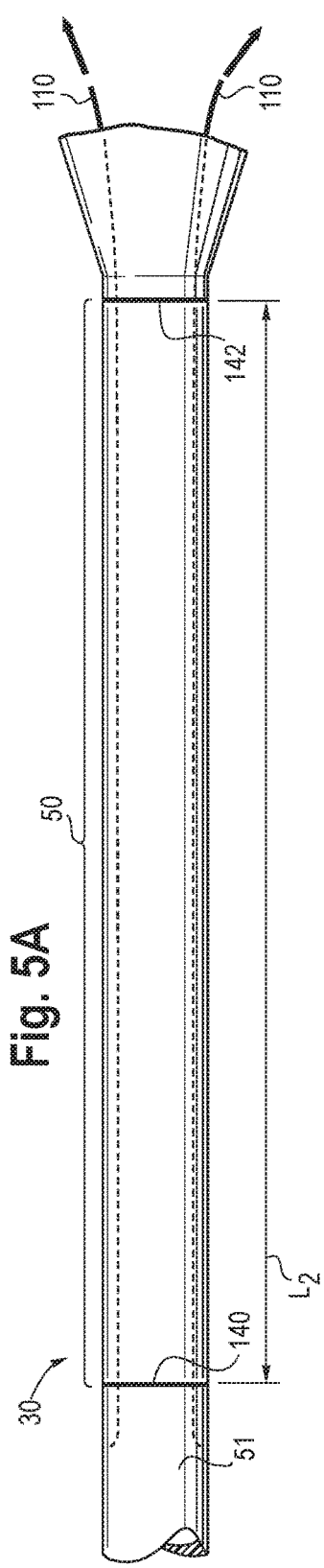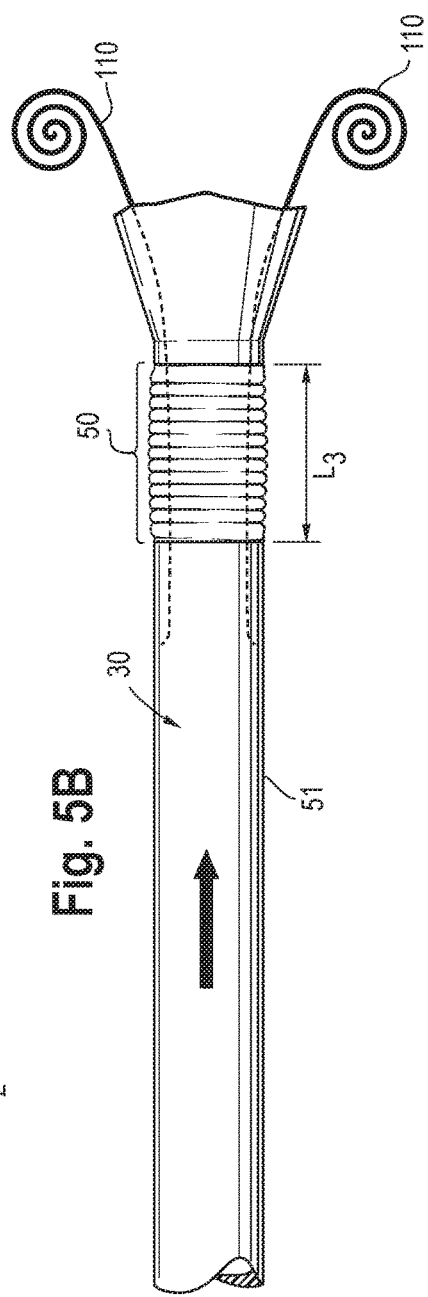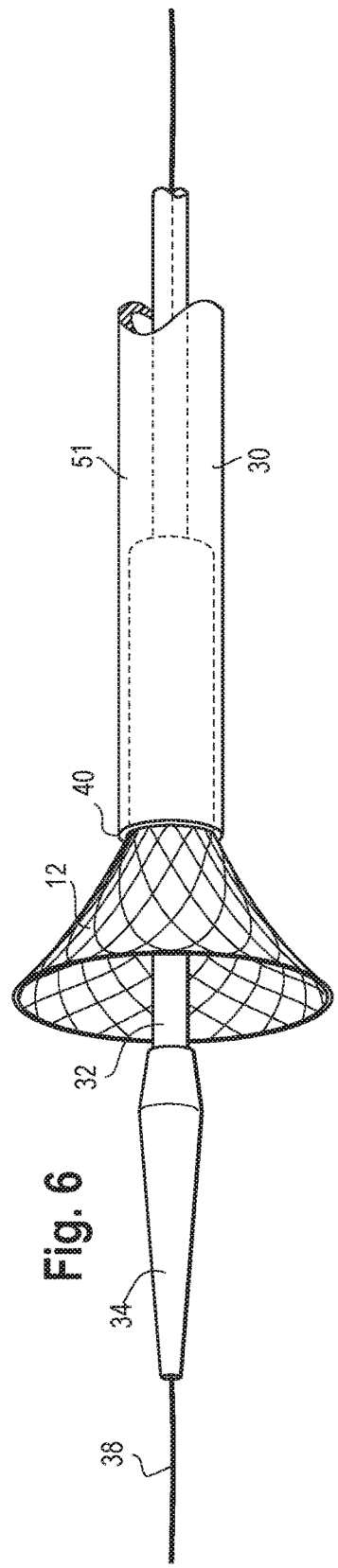

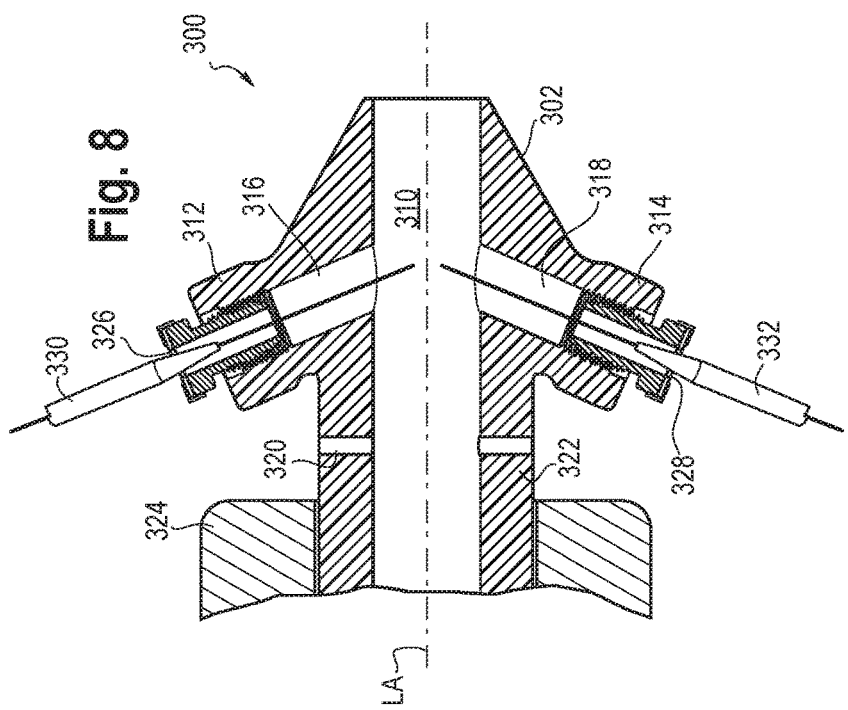
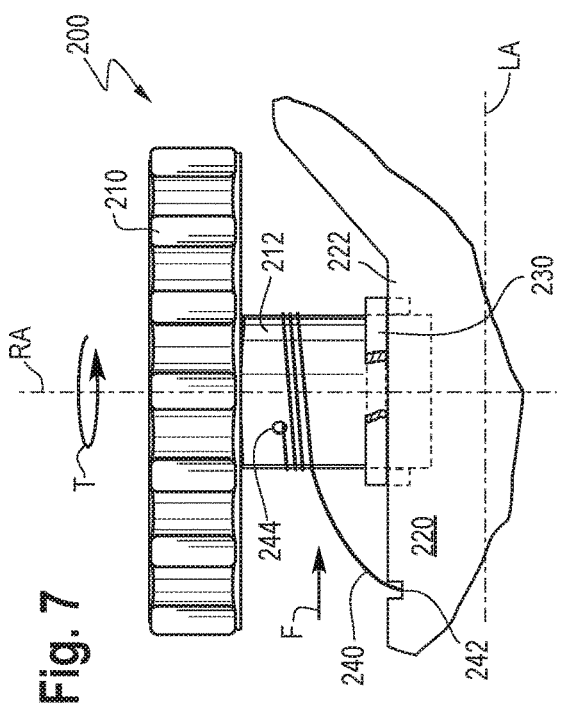

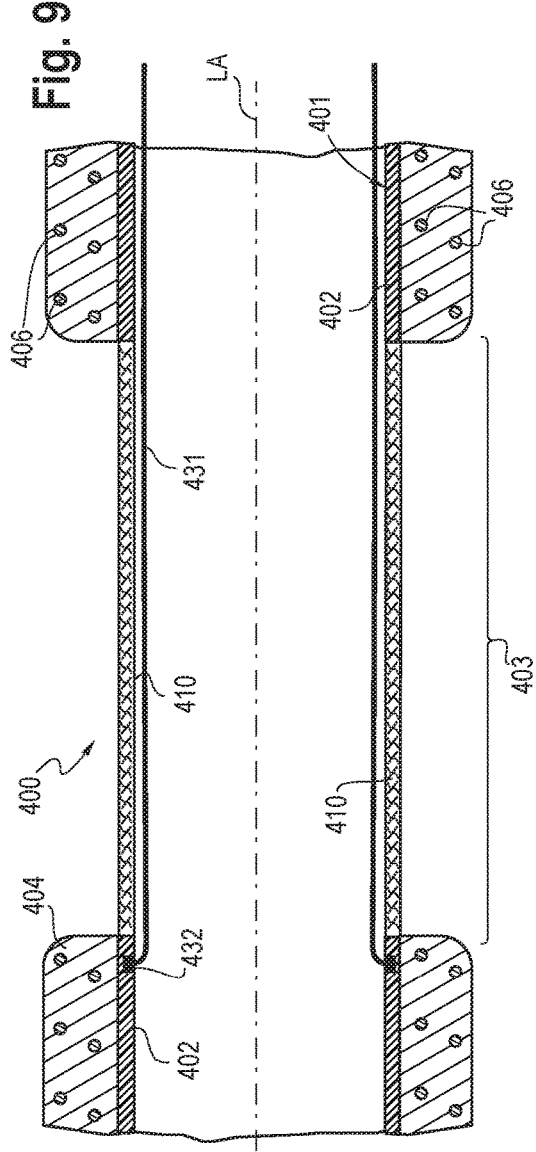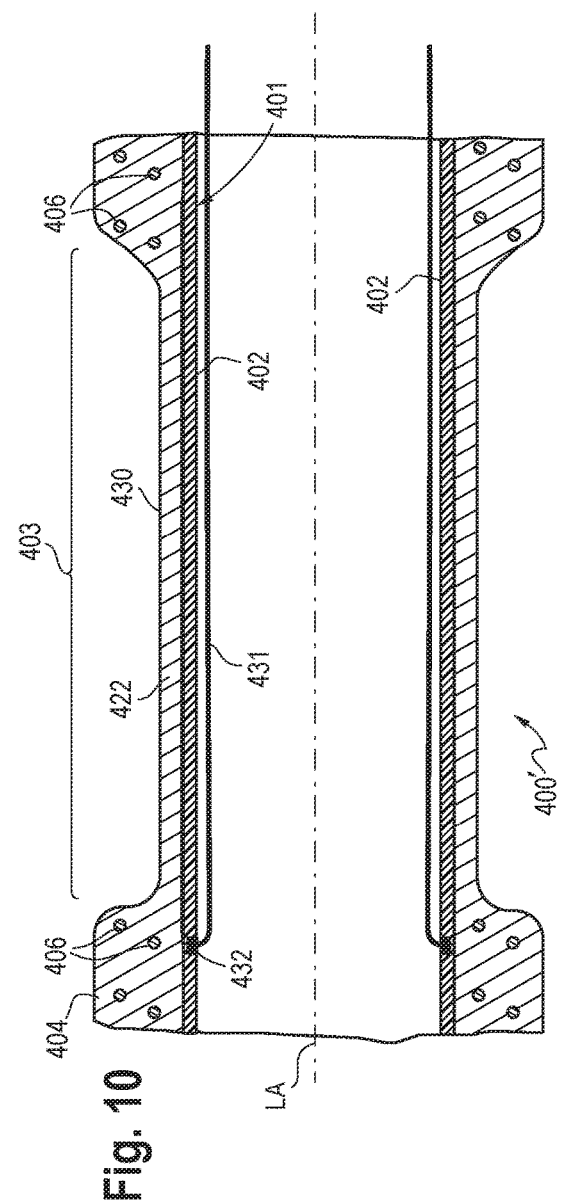

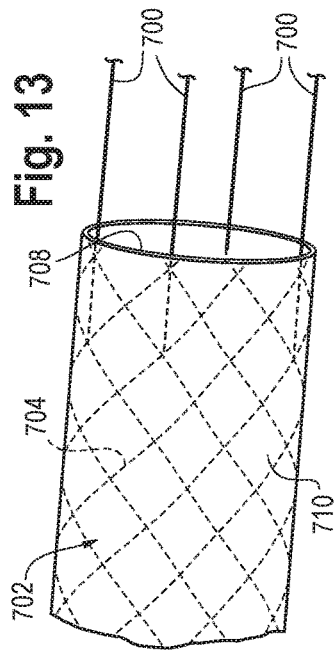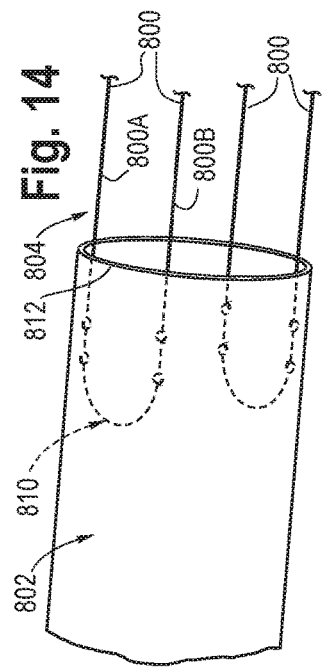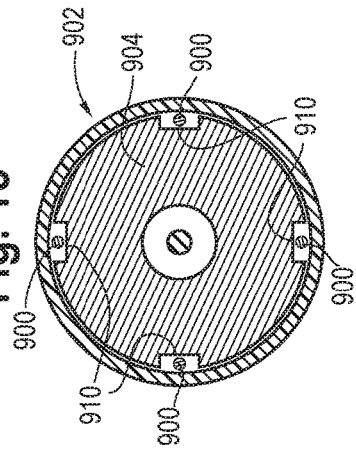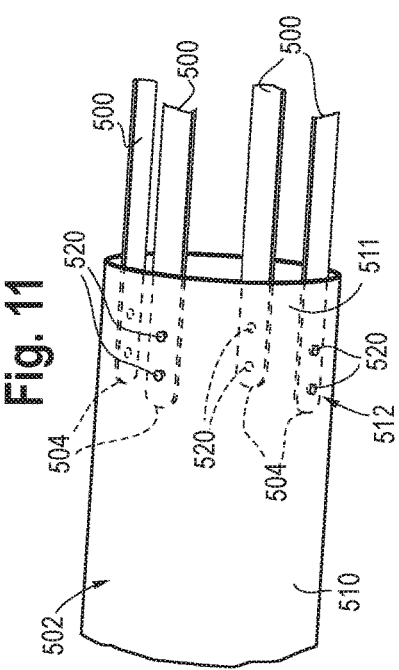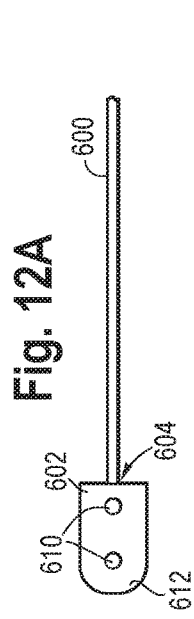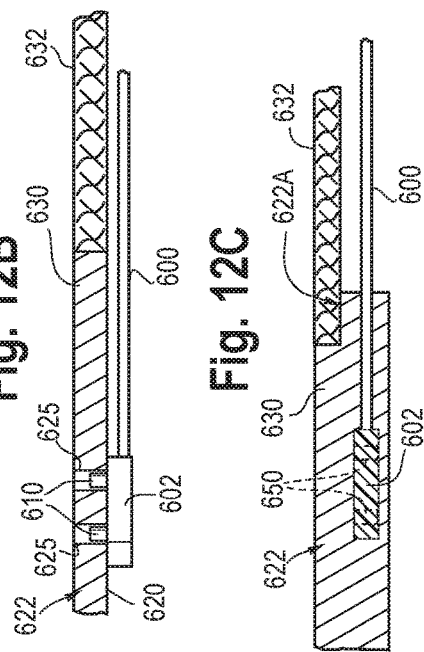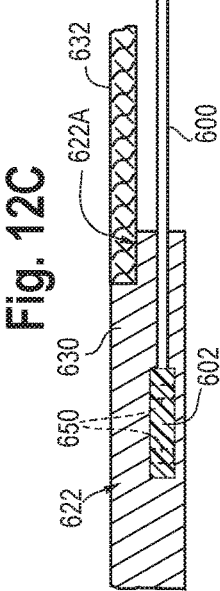

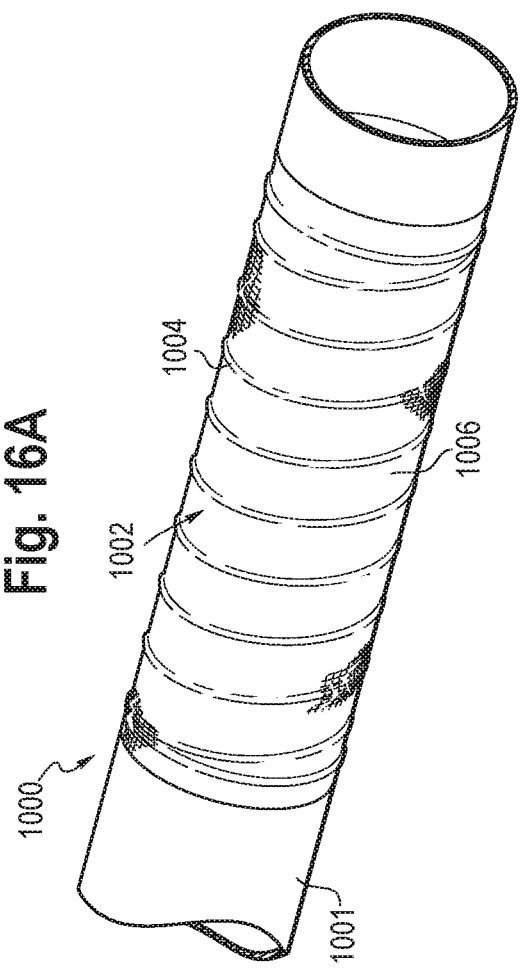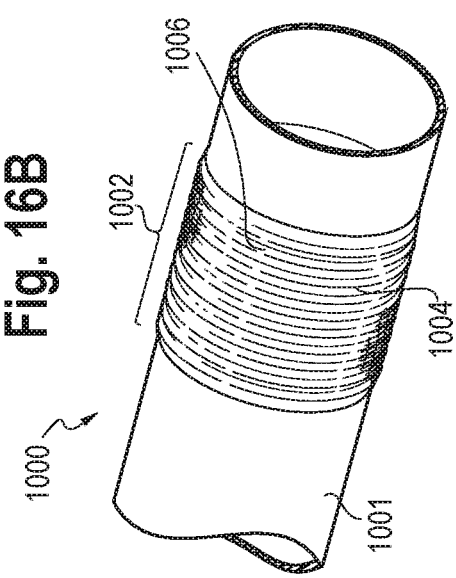

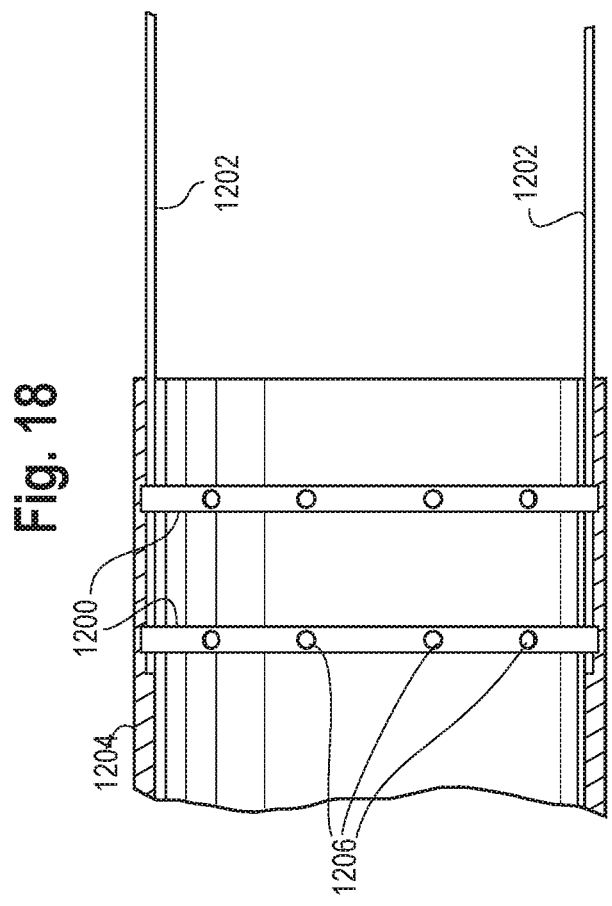
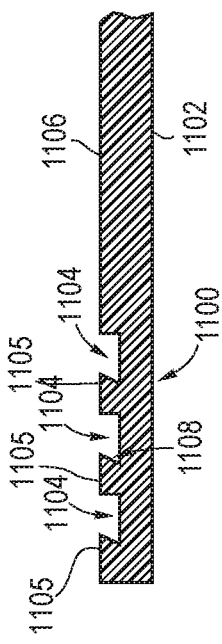
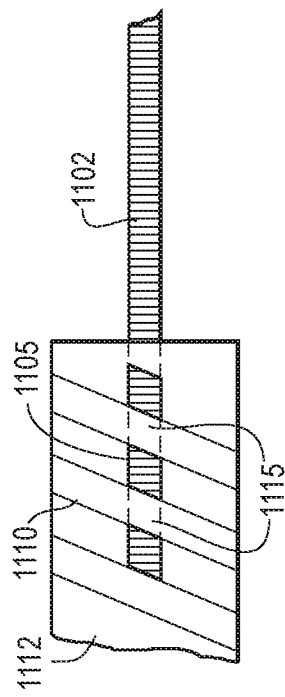

PROSTHESIS DELIVERY SYSTEM WITH AXIALLY COLLAPSIBLE SHEATH

BACKGROUND

The present disclosure relates generally to delivery systems for prosthetic medical devices for implantation within a human or animal body for repair of damaged vessels, ducts, or other physiological pathways, and particularly, to prosthesis delivery systems with a reduced length handle.

The use of delivery devices or introducers employing catheters are used for a variety of medical procedures, including procedures for establishing, re-establishing or maintaining passages, cavities or lumens in vessels, organs or ducts in human and veterinary patients, occlusion of such vessels, delivering medical treatments, and other interventions. For these procedures, an implantable prosthetic medical device is delivered by means of a catheter, often intraluminally. For example, a stent, stent-graft, vena cava filter or occlusion device may be delivered intraluminally from the femoral artery, via a transapical approach and/or using other acceptable delivery locations and methods for deployment of the prosthesis.

For procedures in which a prosthesis or other medical device is implanted into a patient, the prosthesis is normally held on a carrier catheter or cannula of the introducer in a compressed state and then released from the cannula so as to expand to its normal operating state. In many devices, the steps to carry out the implantation may occur, for example, first by retracting an outer sheath away from the loaded prosthesis to allow for its expansion, and then performing further steps, for example, to release one or both ends of the prosthesis, deploy an anchoring stent, or the like. Longer delivery systems are used for aortic treatment, especially those with additional peripheral vessel access sheaths. Longer devices require longer guidewires and other components, and may be more cumbersome and difficult to manipulate. Because there is an increasing complexity and variety of vascular anatomies targeted for treatment, there is a need for improved delivery systems and methods.

SUMMARY

In one example, a prosthesis delivery system including a handle, an inner cannula extending proximally from the handle, and an outer sheath extending proximally from the handle. The outer sheath is coaxially disposed over the inner cannula, and includes an axially collapsible segment and a non-collapsible body disposed proximal to the axially collapsible segment. A pull member is coupled between the handle and the axially collapsible segment or the non-collapsible body of the outer sheath. The handle is operable to retract and wind the pull member such that the axially collapsible segment is collapsed.

In another example, a method of deploying a prosthesis within a body lumen of a patient is described. The method including one or more of the following steps. A step includes introducing a proximal end of a delivery system into a body lumen to a treatment site, the delivery system including a handle, an outer sheath extending proximally from the handle, the outer sheath including an axially collapsible segment, and a pull member coupled between the handle and a portion of the outer sheath, wherein a prosthesis is disposed along a prosthesis retention region defined by the outer sheath and the inner cannula. A step includes removing the outer sheath from the prosthesis at the treatment site by winding a portion of the pull member around a spool portion of the handle such that the axially collapsible segment of the outer sheath is at least partially collapsed and the prosthesis is capable of radial expansion to a deployed configuration.

In another example, a prosthesis delivery system includes a sheath hub having a central barrel. A segment of the central barrel defines a spool portion. A rotatable actuator is coaxially disposed about the central barrel and distal to the spool portion. An inner cannula extends proximally from the sheath hub. The inner cannula is at least partially disposed within a central bore defined by the sheath hub. An outer sheath extends proximally from the sheath hub. The outer sheath is coaxially disposed over the inner cannula. The outer sheath includes an axially collapsible segment. A pull member is coupled between a portion of the outer sheath and the rotatable actuator. The pull member extends through a pull member opening defined by the central barrel. In response to rotating the rotatable actuator in a first direction, the pull member is wound around the spool, the proximal end of the pull member is positioned closer to the handle, and the axially collapsible segment is at least partially collapsed.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIGS. 5A-5B are side views depicting movement of an axially collapsible segment of an outer sheath of the system depicted in FIG. 1 between an extended configuration and a collapsed configuration.

FIG. 6 is a side view depicting radial expansion of a loaded prosthesis after removal of the outer sheath from the prosthesis.

FIG. 7 is a side view depicting another example of a rotatable actuator and spool for winding the pull member.

FIG. 8 is a partial cross-sectional view of another example of a sheath hub including angled side ports.

FIG. 9 is a longitudinal cross-sectional view of a portion of the wall of tubular sheath body of an example of an axially collapsible segment of an outer sheath provided with a delivery system.

FIG. 10 is a longitudinal cross-sectional view of a portion of the wall of tubular sheath body of another example of an axially collapsible segment of an outer sheath provided with a delivery system.

FIG. 11 is a perspective view depicting an example of coupling between a pull member and the outer sheath.

FIG. 12A is a side view depicting an example of a pull member.

FIG. 12B is a partial side and longitudinal cross-sectional side view depicting an example of coupling between pull member depicted in FIG. 12A and the outer sheath.

FIG. 12C is a partial side and longitudinal cross-sectional side view depicting an alternative pull member that may be fused within the matrix of the outer sheath.

FIG. 13 is a perspective view depicting another example of coupling between a pull member and the outer sheath.

FIG. 14 is a perspective view depicting another example of coupling between a pull member and the outer sheath.

FIG. 15 is a transverse cross-sectional view of a catheter body of a delivery system, depicting grooves formed in the inner cannula.

FIGS. 16A-16B are perspective views depicting another example of a prosthesis delivery system with a helical member.

FIG. 17A is a longitudinal cross-sectional side view depicting a proximal end of another example of a pull member.

FIG. 17B is a partial side and longitudinal cross-sectional side view depicting the proximal end of the pull member in FIG. 17A coupled to an example of an outer sheath.

FIG. 18. is a side view depicting another example of a prosthesis delivery system with a reinforcement ring.

DETAILED DESCRIPTION OF THE PREFERRED EMBODIMENTS

Prosthesis delivery systems are disclosed for delivery of implantable prosthetic medical devices within a human or animal body for repair of damaged primary vessels, ducts, or other physiological pathways with branch vessels, ducts, or pathways. In a particular example, the prosthesis may be implanted for suitable treatment of diseases of the aorta such as aortic dissection and aortic aneurysm, and in particular, along the aortic arch or descending aorta distal to the subclavian artery. The delivery systems may include a handle that is configured to shorten the overall length of the delivery system. Short systems may require shorter guidewires and other components, as well as may be easier to use and manipulate. Cannulation with additional access devices may also be made easier with short systems. The handle may be operable to distally retract the outer sheath. The outer sheath may include an axially collapsible segment, which may eliminate length of the handle used conventionally. The axially collapsible segment of the outer sheath may provide the benefit of a significantly shortened portion of the delivery system outside of the body. Length savings may be attributed to the reduced sheath retraction length since the sheath hub does not retract. The handle may include an integrated actuator and one or more integrated pull members coupled to the outer sheath that may be used during the distal retraction of the outer sheath. The pull members may support the axially collapsible segment by providing axial and rotational resistance.

In the present application, the term "proximal" when referring to a delivery device refers to a direction that is farthest away from an operator using a delivery device, while the term "distal" refers to a direction that is generally closest to the operator using the delivery device. The proximal and distal ends of a delivery device may also be referred to as an introduction end of the delivery device and an operator end of the delivery device, respectively. The term "operator end" of the delivery device is that portion of the device that is intended to remain outside of a patient during a procedure. The term "introduction end" of the delivery device, which is opposite to the operator end, is that portion of the device that is intended to be inserted within a patient during a procedure. When referring to the prosthesis itself relative to the delivery device, the proximal end of the prosthesis is that part of the prosthesis closest in proximity to the introduction end of the delivery device and the distal end of the prosthesis is that end that is closest in proximity to the operator end of the delivery device. When referring to the prosthesis relative to placement in the human body of the patient, the ends of the various devices and parts of devices may be referred to as the inflow end (that end that receives fluid first, and the outflow end (that end from which the fluid exits).

Figure 1:
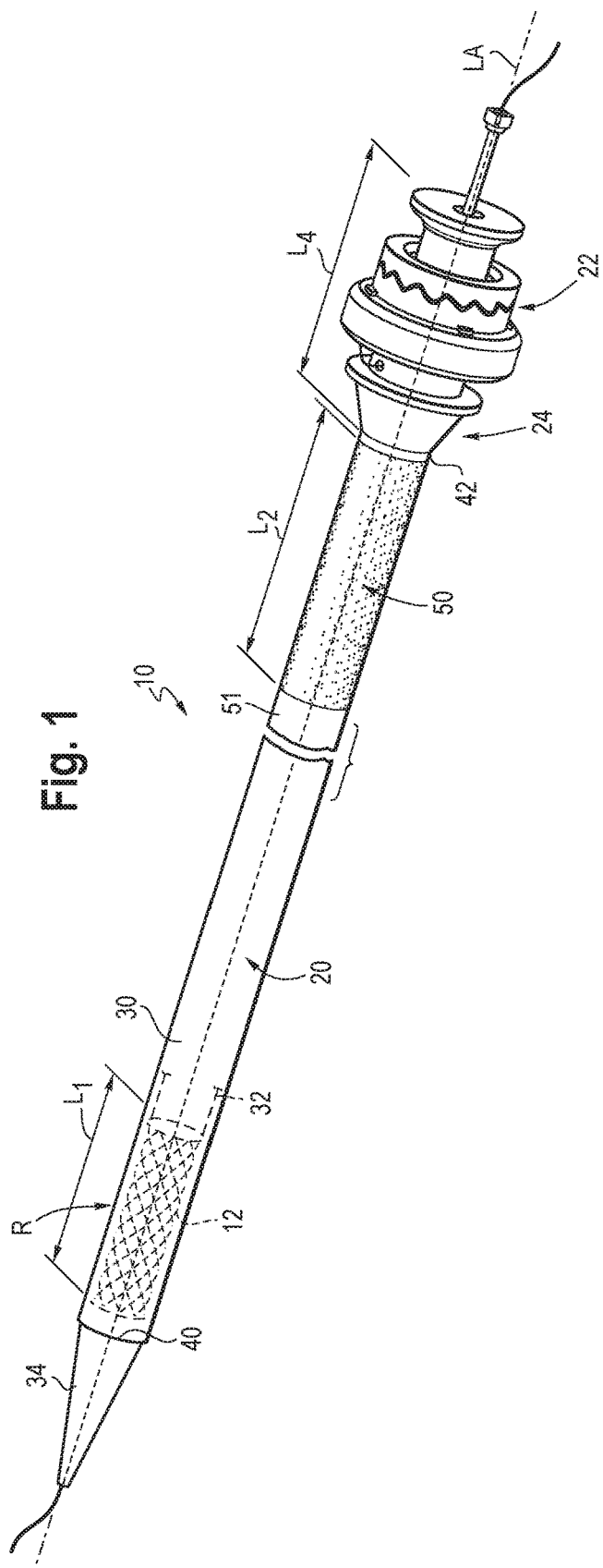
FIG. 1 is a perspective view of an example of a prosthesis delivery system.
Figure 2:
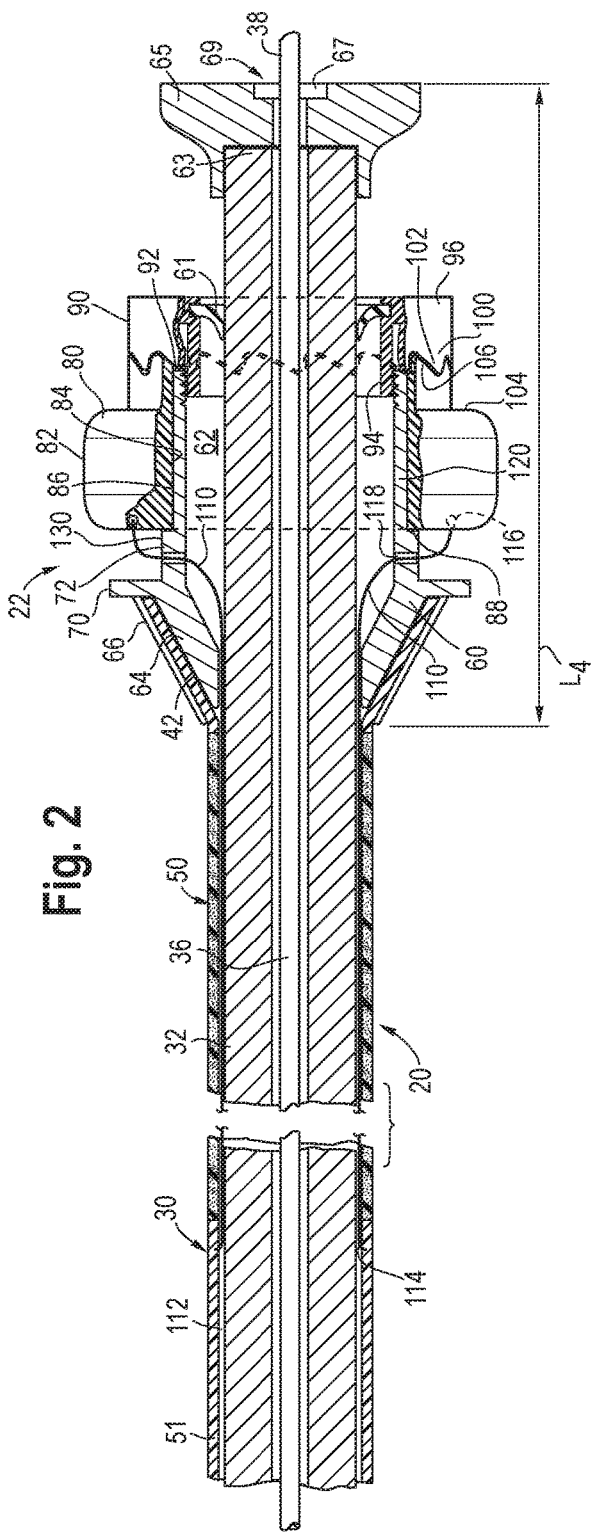
FIG. 2 is a cross-sectional view of a distal end of the system depicted in FIG. 1.

FIG. 1 depicts one example of a delivery system 10 shown having a loaded prosthesis 12. The delivery system 10 includes a catheter body 20 for insertion into the body lumen of a patient and an operable handle 22 disposed at an operator, distal end 24 of the catheter body 20. The catheter body 20 includes an outer sheath 30 coaxially disposed over an inner cannula 32 about a longitudinal axis LA. A nose cone dilator 34 may be disposed at a proximal end of the inner cannula 32. The nose cone dilator 34 and the inner cannula 32 together define a guide wire lumen 36 for receiving a guide wire 38, as shown in FIG. 2. The nose cone dilator 34 and the inner cannula 32 may be bonded together to form a subassembly. The nose cone dilator 34 may be part of a top cap system having a distally extending cap for radially restraining a proximal end of the prosthesis 12. The prosthesis 12 has a longitudinal length L1 in a radially compressed configuration.

An introduction, proximal end 40 of the outer sheath 30 is positioned adjacent to the nose cone dilator 34 and cover the loaded prosthesis 12 when the outer sheath 30 is in the delivery configuration, which is shown in FIG. 1. As will be described, the outer sheath 30 is distally retractable to a deployed configuration to permit at least partial deployment of the prosthesis, which is shown in FIG. 6. The handle 22 is operable to distally retract the outer sheath 30. The outer sheath 30 includes at least one longitudinal segment 50 that is axially collapsible. The axially collapsible segment 50 may be disposed along any region of the outer sheath 30 between the proximal end 40 and a distal end 42 of the outer sheath 30. In one example, the axially collapsible segment 50 is disposed along a distal region of the outer sheath 30 in close proximity to the handle 22. The axially collapsible segment 50 may include a longitudinal length L2 that is at least as long the longitudinal length L1. As described below, the axially collapsible segment 50 may have different configurations. The segment 50 may also include pleats or helical ridges, and may be tapered in diameter such that the segment has an increasingly larger diameter moving from the proximal end to the distal end.

The outer sheath 30 includes a tubular sheath body having a passageway extending longitudinally therethrough. The outer sheath 30 includes a non-collapsible sheath body 51. The non-collapsible sheath body 51 is less axially collapsible than the axially collapsible segment 50. In one example, the non-collapsible sheath body 51 may be referred to as rigid compared to the more flexible axially collapsible segment 50. As will be described, non-collapsible sheath body 51 may include reinforcing members, namely a braid and/or a coil, disposed along the length of non-collapsible sheath body. The non-collapsible sheath body 51 may be disposed distal, proximal, or a combination of both, relative to the axially collapsible segment 50. In one example, the non-collapsible sheath body 51 is shown disposed proximal to the axially collapsible segment 50, making up a substantial length (at least 75%) of the outer sheath.

It is contemplated that the delivery system 10 may include a pusher element. The pusher element may be disposed between the outer sheath 30 and the inner cannula 32 in a coaxial relationship. A proximal end of the pusher element is longitudinally spaced from the nose cone dilator 34 to define an annular prosthesis retention region R where the prosthesis is loaded. In the examples without a pusher element, the annular prosthesis retention region R is an annular region along the proximal end of the outer sheath. The annular prosthesis retention region R sized to receive the longitudinal length L1 of the prosthesis 12 in a radially compressed configuration. For the purposes of this disclosure, the term "inner cannula" will refer to delivery systems having an inner cannula configuration or an inner cannula in combination with a pusher element configuration, as is known.

The handle 22 includes a sheath hub 60 including a central bore 62 defined therein about the longitudinal axis LA for receiving a distal portion of the inner cannula 32, which extends distally beyond the outer sheath 30. A hemostatic sealing element 61 may be housed at the distal end opening of the sheath hub 60. The sealing element 61 may be disposed along the central barrel or the distal end cap. The hemostatic sealing element 61 is configured to allow the passing through of the inner cannula 32 distally beyond the sheath hub 60, while maintaining a fluid tight seal along the surface of the inner cannula 32. The distal end 63 of the inner cannula 32 may include a fluid connector element 65 to allow for flushing of fluids within the guide wire lumen 36. A hemostatic sealing element 67 may be housed at the distal end opening 69 of the fluid connector element 65 to allow the passing through of the guide wire 38 distally beyond the fluid connector element. Sealing elements may also be housed within the nose cone dilator. Each of the sealing elements is configured to prevent back flow of fluid or unintended leakage through the ports. The seal element(s) may be rings, discs or other suitable valving mechanisms made from silicones, rubbers, plastics or other materials.

The sheath hub 60 may include a proximal taper section 64 for insertion into and engagement with the distal end opening of the outer sheath 30. A conical cap 66 may be securely coupled to the proximal taper section 64 to capture the distal end 42 of the outer sheath 30. The conical cap 66 and the proximal taper section 64 may be configured for threadable engagement with one another. The proximal taper section 64 may extend radially outward to a radial flange 70. The sheath hub 60 includes a central barrel 72 extending distally from the radial flange 70. The central barrel 72 may have a reduced outer diameter relative to the radial flange 70. The central barrel 72 may have an internal diameter greater than the inner diameter of the outer sheath 30.

The handle 22 includes an annular rotatable actuator 80 operable for retracting the outer sheath 30. In one example, the rotatable actuator 80 is coaxially disposed about the central barrel 72. The rotatable actuator 80 includes a radial outer surface 82 that may include gripping features such as protrusions or planar portions. A radial inner surface 84 of the actuator 80 may slidably engage an outer surface 86 of the central barrel 72. One or more guiding features such as recesses or flanges may be included along the central barrel 72 for forming a channel for guiding the rotation of the rotatable actuator 80. In one example, the outer surface 86 of the central barrel 72 may include a distal recess that may be a first guiding feature 88 for the actuator 80. A distal end cap 90 may be coupled to a distal end 92 of the central barrel 72. The distal end cap 90 may include a reduced diameter proximal end 94 having an outer diameter sized for insertion into the opening at the distal end 92 of the central barrel 72. The distal end cap 90 may include a distal radial flange 96 having an outer diameter larger than the outer diameter of the central barrel 72. The distal radial flange 96 may be a second guiding feature for the actuator 80, and the first and second guiding features forming the channel of the rotating actuator. The distal end cap 90 and the central barrel 72 may be securely coupled to one another, such as, for example, through threadable engagement or bonded with adhesives.

The rotatable actuator 80 is operable for rotation in a single direction (clockwise or counterclockwise) or both directions about the longitudinal axis LA. The actuator 80 may have a ratcheted configuration for operation with a segment of the handle, as will be described. In one example, the distal end cap 90 and the rotatable actuator 80 are in ratchet engagement with one another. For example, a proximal face surface 100 of the distal end cap 90 may have a plurality of proximally extending teeth 102 annularly arranged and inclined in a first direction. A distal face surface 104 of the rotatable actuator 80 may have a plurality of distally extending teeth 106 annularly arranged and inclined in a second direction. The distally extending teeth 106 are sized and arranged to slidably engage with the proximally extending teeth 102 for effective rotation in one direction only. A biasing member (not shown), such as, for example, a spring or coil, may be coupled to the actuator 80 and proximate to the first guiding feature 88. The biasing member may allow for conditional movement of the ratchet mechanism.

Figure 3:
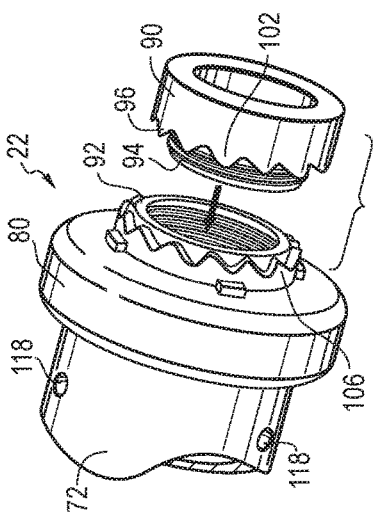
FIG. 3 is a perspective view illustrating assembly of a distal end cap and a rotatable actuator to a central barrel of a sheath hub for the system depicted in FIG.

FIG. 3 shows partial assembly of the handle 22. Here, one example of the rotatable actuator 80 is slid onto the central barrel 72 until engagement with the first guiding feature 88. The proximal end 94 of the distal end cap 90 is then inserted within the opening at the distal end 92 of the central barrel 72. The distally extending teeth 106 are oriented with the proximally extending teeth 102 for effective rotation in one direction only. As described previously, the distal end cap and the central barrel are securely coupled to one another to capture the rotatable actuator, which is rotatable. The use of pawls configured for engagement with one of the teeth may also be used to provide single direction rotation. The use of ratchet release mechanisms may also be used to provide rotation in the direction opposite the direction provided by the teeth. It is contemplated that the ratchet mechanisms may be disposed along the proximal side of the rotatable actuator 80, instead of the distal side as shown. In one example, the central barrel 72 and the rotatable actuator 80 are in ratchet engagement with one another. To this end, the central barrel 72 may receive an annular ring with distally extending teeth may be disposed, and the proximal face of the rotatable actuator may include the proximally extending teeth for ratchet engagement with the distally extending teeth. In another example, the radial inner surface 84 of the actuator 80 may be in ratchet engagement with the outer surface 86 of the central barrel 72.

In FIG. 2, one or more pull members 110 is coupled between the handle 22 and the outer sheath 30. The number of pull members may vary from application to application, and in one example, four pull members may be provided circumferentially disposed away from one another by substantially equal distances. For sake of brevity, a single pull member will be described and its description would apply to the remaining pull members. The pull member 110 is shown disposed internally within the catheter body 20. In one example, the pull member 110 is disposed within the annular lumen 112 defined between the outer sheath 30 and the inner cannula 32. A proximal end 114 of the pull member 110 may be coupled to the outer sheath 30. A distal end 116 of the pull member 110 may be coupled to the rotatable actuator 80. The pull member 110 is shown extending within the central bore 62 of the sheath hub 60, and traversing through a pull member opening 118 defined in the sidewall 120 of the central barrel 72. One or more pull member openings 118 are configured for allowing the pull member 110 to pass externally to the central barrel. The pull member opening 118 is sized and shaped to receive the cross-sectional size and shape of the pull member 110.

Figure 4:
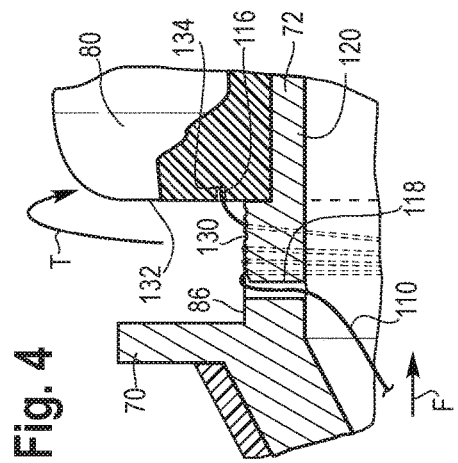
FIG. 4 is a cross-sectional view illustrating operation of the rotatable actuator for winding a pull member about a spool.

A segment of the one or more pull members 110 may be placed in a wound configuration about a spool. In FIG. 4, a segment of the outer surface 86 of the central barrel 72 may define the spool portion 130. The spool portion 130 is shown disposed between the radial flange 70 and the rotatable actuator 80. In this example, the spool portion 130 and the rotatable actuator 80 are in a concentric relationship. The portion of the outer surface 86 along the spool portion 130 may be ribbed, which may be helically arranged, to aid the pull member in the wound configuration. The distal end 116 of the pull member 110 is shown securely coupled to a proximal face 132 of the rotatable actuator 80. In one example, a recess 134 is formed in the proximal face 132, which is sized to receive the distal end 116. A bonding adhesive is applied within the recess and cured to fix the position of the distal end 116 within the recess 134. Due to tension placed on the pull members due to the torque applied to the rotatable actuator 80 for withdrawal of the outer sheath, other coupling means are contemplated to secure the distal end 116. For example, the recess may be formed further into the handle than what is show, and in some instance, entirely through the handle width, which may allow for more bonding surface with the adhesive. It is further contemplated that the pull member has an enlarged proximal end sized larger than the recess such that the pull member is threaded into the recess (now through opening) from the distal side.

When the outer sheath 30 is in the delivery configuration, the prosthesis 12 is maintained in the radially compressed delivery configuration and the axially collapsible segment is in its extension configuration defining the longitudinal length L2, as shown in FIG. 5A. The axially collapsible segment 50 is movable to its axially collapsed configuration to a longitudinal length L3, as shown in FIG. 5B, which is less than length L2. In some examples, the length L3 may be about ⅐ the length of L2. Other relative sizes for length L3 may be chosen depending on the construction of the axially collapsible segment, among other factors. It is contemplated that the difference in lengths L2 and L3 may be at least as long as the length L1. In one example, as shown in FIGS. 1-2, the longitudinal length L4 of the handle 22 is less than the difference in lengths L2 and L3, which is the retraction length of the outer sheath provided for deployment of the prosthesis. The longitudinal length L4 of the handle is measured between the proximal end of the sheath hub and the distal end cap, which may also include the distal end of the connector, as shown. Shorter handles may be easier to manipulate and may require shorter components. FIG. 5B also illustrates an example of the sheath hub without an actuator, but instead the pull members would be routed through the sheath hub and manually curled or heat set to curled shape or otherwise withdraw to activate distal retraction of the outer sheath.

Movement of the axially collapsible segment 50 may be performed by distal retraction of the one or more pull members 110. Distal retraction of the pull member 110 to bring a proximal end 140 of the axially collapsible segment 50 closer to a distal end 142 of the segment 50. This may include bringing the proximal end 114 of the pull member 110 in closer proximity to the handle 22. This operation removes the distal end 40 of the outer sheath 30 from the loaded prosthesis 12 to allow the prosthesis 12 to move from the radially compressed delivery configuration to the radially expanded deployed configuration, as shown in FIG. 6. Distal retraction of the pull member 110 may occur once a torque T is applied to the rotatable actuator 80 in the first direction, as shown in FIG. 4. The torque is translated as a longitudinal retraction force F suitable to distally retract the pull member 110 through the pull wire opening 118, thereby beginning axial collapse of the axially collapsible segment 50. Continued rotation of the rotatable actuator 80 may begin winding the pull member 110 about the spool portion 130 of the central barrel 172 as the axially collapsible segment 50 continues to shorten. The prosthesis 12 begins to radially expand as the proximal end 40 of the outer sheath 30 is removed distally along the prosthesis 12. There may be a point during the rotation of the actuator 80 when high effort is required by the physician. This is generally an indication that the axially collapsible segment 50 has reached its axially collapsed configuration.

Other mechanisms for distal retraction of the pull member 110 are contemplated. In one example, the spool portion is in eccentric relationship with the central barrel. FIG. 7 depicts another example of the handle (now referred to as handle 200) for use in the delivery system 10 and the shortening of the axially collapsible segment 50. Here, the rotatable actuator 210 and the spool 212 are securely fixed to one another such that rotation of the actuator 210 causes rotation of the spool 212 about a rotation axis. The rotation axis RA may be perpendicular to the longitudinal axis LA. The spool 212 is shown extending normal to the outer surface 220 of the central barrel 222. A bearing or support element 230 may be placed around the spool 212 and securely coupled to the outer surface 220 of the central barrel 222. In one example, an opening may be formed in the sidewall of the central barrel 222, which is sized to receive a portion of the spool. The bearing 230 alone, or in addition to a separate ratchet mechanism, may be configured for ratchet engagement with the spool 212 for effective single direction rotation. The pull member 240 is shown traversing through the pull member opening 242 such that the distal end 244 of the pull member 240 may be securely coupled to the spool 212. Distal retraction of the pull member 240 may occur once the torque T is applied to the rotatable actuator 210 in the first direction. The torque is translated as the longitudinal retraction force F suitable to distally retract the pull member 240 through the pull wire opening 242, thereby beginning axial collapse of the axially collapsible segment 50. Continued rotation of the rotatable actuator 240 may begin winding the pull member 240 about the spool 212 until the prosthesis is deployed, as described herein. Some handles may be configured without a rotatable actuator. In these examples, the operator may grab the pull member extending out of the pull member openings with hands or a tool, such as pliers, and apply the retraction force manually.

FIG. 8 depicts another configuration of the sheath hub (now referred to as sheath hub 300) with additional side ports, generally for allowing the passing through of auxiliary devices, such as catheters, access sheaths, guidewires while the outer sheath is within the body lumen. The auxiliary devices may be useful, for example, when the prosthesis 12 is a fenestrated stent graft having fenestrations in alignment with branch vessels. Such auxiliary devices may be preloaded (that is, embedded within the outer sheath prior to delivery to the body lumen, or the devices may be inserted after the outer sheath's delivery to the body lumen. The sheath hub 300 may include the proximal taper section 302 for insertion into and engagement with the distal end opening of the outer sheath 30. The conical cap (not shown) may securely couple the outer sheath to the proximal taper section. In addition to the central bore 310, the sheath hub 300 may include one or more angled side ports (two shown side ports 312 and 314). Each of the side ports define auxiliary lumens 316, 318, respectively, in fluid communication with the central bore 310. The side ports 312, 314 may be positioned proximal to the pull member opening 320 formed in the central barrel 322 and the rotatable handle 324, as shown. The pull member openings 320 may be circumferentially offset from the side ports 312, 314 in order to space the respective pull members and auxiliary devices annularly within the central bore. In another example, the side ports 312, 314 may extend from the central barrel and be positioned distal to the rotatable handle.

Although the inner cannula may be removable from the outer sheath to allow access for the auxiliary devices, the inner cannula (not shown) may be configured to reside with the outer sheath. Here, the inner cannula may include two side apertures that open from the side of the inner cannula into the respective auxiliary lumens 316, 318. These side apertures are sized and shaped to provide an uninterrupted lumen from the access port 312 for a first access sheath into the outer sheath 30 and from the access port 314 for a second access sheath into the outer sheath 30. The access port 312 is shown having a hemostatic sealing element 326 for a first access sheath 330, and the access port 314 is shown having a hemostatic sealing element 328 for a second access sheath 332.

FIGS. 9-10 are longitudinal cross-sectional views of a portion of the wall of tubular sheath body of examples of the outer sheath provided with the delivery system 10 (now referred to as outer sheath 400 in FIGS. 9 and 400' in FIG. 10). The non-collapsible sheath body 401 of the outer sheath 400 or 400' may include an inner liner 402. A polymeric outer jacket 404 may be mechanically connected to a radially outer surface of the inner liner 402, such as, for example, the outer jacket material entering through spaced filaments of reinforcing members 406 when fitted around the inner liner 402. The inner liner 402 may include a lubricious material, and, in one example, a fluoropolymer such as polytetrafluoroethylene (PTFE). The inner diameter of the inner liner 402 may be uniform the entire length of the passageway. In one example, the outer surface of the inner liner 402 is chemically etched or mechanically roughened in well-known manner for enhancing bonding between the inner liner 402 and the outer jacket 404. The outer tube jacket 404 may be formed of any well-known polymer commonly used for such purpose. In one example, the outer jacket 404 includes a heat formable polyamide material, such as nylon, or a polyether block amide (PEBA), which melts upon heating, such that portions flow between the respective filaments or turns of the reinforcing members 406, such as the coils or braid, and bond to the roughened outer surface of the inner liner 402. FIG. 9 depicts an example of the outer sheath 400 having an interrupted inner liner, that is, the inner liner terminates at the axially collapsible segment 403.

The reinforcing members 406 may include a braid including a plurality of crossed filaments of circular, flat, elliptical, or other cross-sections, made of medical grade metal or metal alloy. Non-limiting examples of such materials include stainless steel, and shape memory alloys such as nitinol, a nickel-titanium alloy. The braid may be formed with varied numbers, and pitches, of crossed wires, which number of wires and pitch may be varied within segments of a particular sheath, all in accordance with known techniques. The reinforcing members may include a coil, alone or in additional to the braid, including a medical grade metal or metal alloy, such as stainless steel, or a shape memory composition such as nitinol. The coil may be formed from flat wire, although a coil formed from other compositions and having other cross-sections may be substituted in an appropriate case. The coil may be wrapped, wound, compression fitted, or otherwise applied around the inner liner 402. The coil in the outer sheath may minimize the possibility of the sheath kinking, and/or to minimize ovalization of the sheath lumen during bending of the sheath. The braid, on the other hand, is typically utilized when it is desired to impart stiffness, pushability, or torqueability to the sheath. Such properties are advantageous when maneuvering a lengthy sheath or catheter into remote anatomy. Placement of such coils and/or braids along the outer sheath may be appreciate by those skilled in the art. The non-collapsible sheath body 401 may include the reinforcing members, and the axially collapsible segment 403 may remain free of the reinforcing members. In another example, the axially collapsible 403 may include a reinforcing member, such as a braid, that exhibits suitable axial tensile strength and longitudinal compressibility for the axially collapsible segment 401.

FIG. 9 depicts the axially collapsible segment 401 of the outer sheath 400 being formed from a woven structure 410 that is mechanically coupled to the non-collapsible sheath body 401. The woven structure 410 may be lined along the outer surface and/or the inner surface with a lining similar to the inner liner 402 described herein to prevent leakage along the segment. In another example, the woven structure may be coated along the outer surface and/or the inner surface by dipping, spraying, brushing a coating solution such as one of the polymers described herein. The strands or filaments used to form the woven structure may provide suitable axial tensile strength and longitudinal compressibility for the axially collapsible segment 401. The axially collapsible segment 401 may utilize suppleness of the woven structure without sacrificing integrity or strength of the outer sheath.

The woven structure 410 may include any kind of weave of textile strands and/or shape memory element strands interlaced with any various over and under configurations. For example, the woven fabric weave may include, but is not limited to, weaves such as plain weaves, basket weaves, rep or rib weaves, twill weaves (e.g., straight twill, reverse twill, herringbone twill), satin weaves, and double weaves (e.g., double-width, tubular double weave, reversed double weave). Determination of which primary weave is most appropriate may be based on a variety of factors, including intended clinical application, desired properties of the woven fabric, weave type, and strand properties such as the size or denier of the strand and the shape of the strands.

The textile strands used in the woven structure 410 may include any biocompatible material. The textile strands may be natural, synthetic, or manufactured. For example, biocompatible materials from which textile strands may be formed include, but are not limited to, polyesters, such as poly(ethylene terephthalate); fluorinated polymers, such as polytetrafluoroethylene (PTFE) and fibers of expanded PTFE; and polyurethanes. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer. Materials used for the shape memory element strands in the woven structure 410 need only be biocompatible or able to be made biocompatible. Suitable materials for the shape memory element strands include shape memory metals and shape memory polymers. Suitable shape memory metals include, for example, TiNi (Nitinol), CuZnAl, and FeNiAl alloys. Particularly preferred are "superelastic" metal alloys. Superelasticity refers to a shape memory metal alloy's ability to spring back to its austenitic form from a stress-induced martensite at temperatures above austenite finish temperature. The austenite finish temperature refers to the temperature at which the transformation of a shape memory metal from the martensitic phase to the austenitic phase completes.

The woven structure may be coupled to the non-collapsible sheath body 401 by various coupling processes. One or both ends of the tubular woven structure 410 may be inserted between the outer jacket and the inner liner prior to heat setting in order to bond or fuse the tubular woven structure with the non-collapsible sheath body 401. In another example, one or both ends of the tubular woven structure 410 may be inserted over or within the edge of the non-collapsible sheath body 401 of the outer sheath. After insertion and positioning, an adhesive, such as a heat-cured adhesive or cyanoacrylates, may be applied and eventually cured to bond the structures together. In addition to any one of the disclosed coupling processes, a filament or wire made from any one of the biocompatible materials described herein may be sewn or otherwise threaded in and out of the sidewall of the non-collapsible sheath body 401 and the sidewall of the tubular woven structure for added coupling strength.

In FIG. 10, the axially collapsible segment 403 of the outer sheath 400' may have a reduced wall thickness segment 430 along the sidewall of the outer sheath. The reduced wall thickness segment 430 may be formed from the inner liner 402 alone. In another example, the reduced wall thickness segment 430 may be formed from the outer jacket segment 404 without any reinforcing members 406. In another example, the reduced wall thickness segment 430 may be formed from a second outer jacket segment 422, as shown, having a sidewall thickness less than the outer jacket 404 used for the non-collapsible sheath body 401. The second outer jacket segment 422 may be made from materials described above in relation to the outer jacket 404. The outer surface may be pre-configured with pleats or other features such as corrugated, for enhancing the collapsible of the section. A reinforcing member may be added to suitable axial tensile strength and longitudinal compressibility for the axially collapsible segment 403 of the outer sheath 400' for suitable tensile strength and collapsible properties.

The resistance imparted by the prosthesis 12 upon the interior wall of any one of the disclosed outer sheaths upon deployment may cause the outer sheath to stretch in the longitudinal direction as the outer sheath is withdrawn from around the prosthesis. Due to the inherent structure of the woven structure 403 or the braid, e.g. made up of woven filaments, when employed as a reinforcing member in the in the axially collapsible segment 403, the woven structure 403 or braid in the axially collapsible segment 403 may be less susceptible to axial stretching. The woven structure 403 or braid may also provide tensile strength for pulling and pushing the outer sheath.

FIGS. 9-10 show one example of the pull members 431 coupled to the non-collapsible sheath body 401 proximal to the beginning of the axially collapsible segment 403. The proximal end 432 of the pull member 431 is bonded or otherwise securely coupled to the inner surface of the outer sheath 400 or 400'. The inclusion of the pull members 431 along the axially collapsible segment 403 may provide added tensile strength and torqueability transference to the axially collapsible segment 403. The pull members 431 may allow for the omission of reinforcing members 406 along the axially collapsible segment 403 and/or the capability of selecting woven structure 410 and/or thickness of the reduced wall thickness segment 430 that provide greater axially compressibility than otherwise possible. To this end, the pull members 431 may be configured to be locked into position during the delivery of the delivery system and unlocked to allow for distal retraction. The rotatable handle with the ratchet engagement as described herein provide the pull members that locking capability. When locked, the pull members provide axial struts along the axially collapsible segment 403 of the outer sheath. Other locking mechanisms, such as common to trigger wire configurations, may also be used as understood by those skilled in the art.

Examples of coupling and/or integrating of any of the disclosed pull members within any one of the disclosed outer sheaths, will now be described. Any one of the disclosed pull members may comprise a biocompatible polymer, metal or metal alloy. In one example, the pull member is a wire member having a cross-sectional shape of a circular or elliptical. In another example, the pull member is a ribbon having a rectangular or elliptical cross-sectional shape. The pull member may impart additional rotational and axial strength to the collapsible section for improved axial force and torque transferability between the handle and the non-collapsible segment. A plurality of pull members may be provided at equiangular distances relative to one another. In one example, two pull members may be circumferentially spaced from one another by about 180 degrees. In another example, three pull members may be circumferentially spaced from one another by about 120 degrees. In another example, four pull members may be circumferentially spaced from one another by about 90 degrees. It is contemplated that additional pull members may be placed at various angles from one another.

FIG. 11 shows an example of coupling and/or integrating the pull member 500 within the outer sheath 502, which may be any one of the disclosed outer sheaths, will now be described. The proximal end 504 may be coupled to the non-collapsible sheath body 510 and/or the axially collapsible segment 511. The proximal end 504 of the pull member 500 may be coupled to a distal end 512 of the non-collapsible sheath body 510. One or more bonding ports may be formed in the sidewall of the non-collapsible sheath body 510, for example, near its distal end 512. The bonding ports 520 may be through bores. The proximal end 504 of the pull member 500 may be placed along the inner surface of the outer sheath 502 and aligned in an overlapping relationship with the bonding ports 520. An adhesive, such as described above, is applied to the pull member through the bonding ports for securely fixing the proximal end 504 to the non-collapsible sheath body 510. In addition to, or instead of, the adhesive, sutures or wire may be utilized to stitch the proximal end 504 to the outer sheath 502. FIG. 11 shows the pull member 500 having a ribbon configuration with a rectangular cross-sectional shape. The distal end of the pull member 500 is then routed through the outer sheath into the handle, as described above.

FIG. 12A shows another example of the pull member, now referred to as pull member 600, having a tab 602 defining the proximal end 604 of the pull member 600. The tab 602 may provide a larger surface area than what may be provided by the proximal end of the pull member without the tab. In one example, the proximal end 604 for example, the tab 602, may include protrusions 610 extending away from a surface 612 of the tab 602. The protrusions 610 are sized and shaped to fit within the bonding ports of the outer sheath to provide additional axial strength for the coupling. In FIG. 12B, the tab 602 is placed along the inner surface 620 of the outer sheath 622 and the protrusions 610 are shown extending within the bonding ports 625 formed in the non-collapsible sheath body 630 proximal to the axially collapsible segment 632. The protrusions 610 may be fixed securely within the bonding ports 625 with an adhesive, as described above. FIG. 12C depicts features that may be adopted by the other example configurations shown. In an example, the proximal end of the pull member 600 may be heat fused within the matrix of the outer sheath 622. In an example, the axially collapsible segment 632 may be sized to fit over a neck region 622A formed in the outer sheath 622. This configuration may provide a consistent profile along the outer surface of the outer sheath and provide an annular gap between the axially collapsible segment 632 and the inner cannula (not shown). The tab 602 in FIG. 12C is shown disposed within the outer sheath matrix. The proximal end of the pull member, such as for example, the tab 602, may include one or more apertures 650 to allow flow of polymer during heat fusing of the tab within matrix. The tab 602 may be polymer, metal or metal alloy. In one example, the tab 602 may have a plurality of apertures formed in a metal structure. The distal end of the pull member 600 is then routed through the outer sheath into the handle, as described above. In another example, the protrusions may extend away from the ribbon configuration of the pull member. In another example, the pull member may be attached to the outer sheath without the tab.

In one example, the profile of the axially collapsible segment in the extension configuration is no larger than the profile of the non-collapsible sheath body, as shown, for example, in FIGS. 2 9, 10, 12B, 12C. The profile may be defined as the shape and/or size of a body. In another example, the circular and the cross-sectional area of the axially collapsible segment in the extension configuration is no larger than the cross-sectional area and has a similar shape of the non-collapsible sheath body.

FIG. 13 depicts another example of the pull member, now referred to as pull member 700, where the axially collapsible segment is omitted from the outer sheath 702 for clarity. In one example, the pull member 700 is integral with one or more of the reinforcing members 704 provided within the non-collapsible sheath body 710. Here, the reinforcing members 704 may be a braid where the strands or filaments are cut or unwoven such that the strands or filaments extend from the sidewall 708 of the non-collapsible sheath body 710 to define the pull member. The distal end of the pull member 700 is then routed through the outer sheath into the handle, as described above.

FIG. 14 depicts another example of the pull member, now referred to as pull member 800, where the axially collapsible segment is omitted from the outer sheath 802 for clarity. In one example, a pair of first and second pull members 800A, 800B may be formed from a single member 804, such as a wire member. The respective ends of the single member 804 may be routed through the outer sheath into the handle, as described above. A bend or transition loop 810 is formed along an intermediate region of the single member 804. The bend 810 may be inserted within the edge 812 of the outer jacket and the inner liner prior to heat forming of the sheath wall of the non-collapsible sheath body. In another example, a pair of first and second pull members 800 may be formed a pair of wire members coupled at the proximal ends to form a single structure. The respective distal ends of the pull members 800 that now form ends of the single structure may be routed through the outer sheath into the handle, as described above. A bend or transition loop may be formed at the coupling of the proximal ends, which is to be inserted within the edge of the outer jacket and the inner liner prior to heat forming of the sheath wall.

FIG. 15 depicts a cross-sectional view of another example of the outer sheath 902 where the pull members 900 are located. The inner cannula 904, or in some instances the pusher element, may having longitudinal grooves 910 formed therein. The grooves 910 define channels for the pull members 900 to slide within. In one example, the grooves 910 are shown open ended to the annular lumen. In another example, the grooves 910 are closed off in a manner to define internal lumens within the inner cannula. Alternatively, any one of the disclosed pull members may be free floating within the outer sheath, and may be routed within the annular lumen 112 as shown in FIG. 2.

FIGS. 16A-16B depict another example of a portion of examples of the outer sheath provided with the delivery system 10 (now referred to as outer sheath 1000). The outer sheath 1000 includes the non-collapsible sheath body 1001 and the axially collapsible segment 1002. The axially collapsible segment 1002 may include a helical member 1004, such as, for example, to provide radial reinforcement along the axially collapsible segment 1002. The helical member 1004 may include a spring structure or ribbon structure formed from a polymer, metal or metal alloy wound helically. The helical member 1004 may be disposed along the inside, the outside or disposed within the sheath body 1006 of the axially collapsible segment 1002. Types of sheath body materials are described herein, for example, with FIGS. 9-10. FIG. 16A shows the axially collapsible segment 1002 in its extension configuration. FIG. 16B shows the axially collapsible segment 1002 in its axially collapsed configuration by movement of the pull member(s) as described herein. The helical member 1004 may be further configured to facilitate movement and/or control of the outer sheath retraction. In one example, the helical member 1004 may be biased in the extended positon. The biasing may provide greater controllability to the physician during retraction. In another example, the helical member 1004 may be biased in the collapsed positon. This biasing configuration may allow for less effort of physician during retraction as the helical member seeks its biased position.

FIGS. 17A-17B show the proximal end 1100 of another example of the pull member 1102. The proximal end 1100 (or in some examples the tab) is configured for coupling with the reinforcing members in the outer sheath, which may also facilitate the tensile strength of the pull members. The proximal end 1100 or tab (not shown) may be roughened, cut, or notched to increase frictional engagement with the reinforcing members. FIG. 17A depicts the proximal end 1100 including one or more notches 1104 machined or otherwise formed in an upper surface 1106 or the lower surface to define protrusions 1105. An undercut 1108 may be formed along the base of the protrusions 1105 to form an angled surface to aid in capturing and retaining the elements of the reinforcing member. The notches 1104 may be rectangular. As shown in FIG. 17B, the proximal end 1100 of the pull member 1102 may be coupled to the reinforcing member 1110 formed in the outer sheath 1112, which may be the non-collapsible segment. The axially collapsible segment is omitted for clarity. The elements 1115 of the reinforcing member are shown disposed within the notches 1105, which may be a loose fit or a tight fit to form an interlocked relationship. When the reinforcing member 1110 is a helical member or coil formed in the outer sheath 1112, the notches 1104 may be angled to align with the corresponding angled elements for the reinforcing member. Similar to what is described in relation to FIG. 12C, the proximal end of the pull member 1102 may be heat fused with the outer sheath 1112.

FIG. 18 depicts the use of one or more reinforcement rings 1200 for coupling the pull members 1202 to the outer sheath 1204, which may also facilitate the tensile strength of the pull members 1202. The reinforcement ring 1200 are sized to receive the inner liner (when employed) and the pull members 1202. Apertures 1206 may be formed along the circumference of the reinforcement ring 1200 to allow flow of polymer during heat fusing of the rings and pull member within the outer sheath matrix. Similar to the description in relation to FIGS. 17A-17B, the proximal end of the pull members 1202 may be may be roughened, cut, or notched to increase frictional engagement with the reinforcing ring(s) 1200. The reinforcing rings 1200 may be casted, machined, laser cut, molded or otherwise formed from a polymer, metal or metal alloy.

The outer sheath may be constructed in the following manner. Initially, the inner liner is placed on a suitably-sized mandril. Generally, the mandril will have an outer diameter substantially the same as the inner diameter of the inner liner to insure a close tolerance between the two. A braid is cut to a length such that the braid will extend along a suitable length of the sheath body. The ends of the braid may be pre-treated to control fraying. The braid may be slid over the liner at one side (proximal) of the mandril. The coil is transferred over the distal end of the mandril. The outer jacket material is then slid over the mandril/liner/reinforcements (braid+coil), and the entire assembly is placed in a heat shrink envelope, such as, for example, made of fluorinated ethylene propylene (FEP), as long as the melt temperature of the material used for the outer jacket is lower than that of the heat shrink enclosure. The heat shrink enclosure and contents are placed in an oven and heated (typically at about 385° F. (196° C.) when FEP is used as the heat shrink and a polyether block amide is used as an outer jacket material) for a suitable period of time to melt the outer jacket material such that it flows between the braid filaments and the coil turns as described. After removal from the oven, the entire assembly is cooled, and the FEP envelope is cut away. These processes may be modified accordingly with the additional steps described above, such as, for example, but not limited to the formation of the axially collapsible segment and the coupling and/or integration of the pull members.

Prosthesis 12 may be any device that is introduced temporarily or permanently into the body for the prophylaxis or therapy of a medical condition. For example, such medical devices may include, but are not limited to; endovascular grafts, stents, stent grafts, balloon catheters, meshes, vascular grafts, stent-graft composites, filters (for example, vena cava filters), vascular implants, tissue scaffolds, myocardial plugs, valves (for example, venous valves), various types of dressings, endoluminal prostheses, vascular supports, or other known biocompatible devices.

The delivery systems described herein may need various other components in order to obtain a delivery and deployment system that is optimally suited for its intended purpose. These include and are not limited to various outer sheaths, pushers, trigger wires, stoppers, guide wires, and the like. For example, the Zenith® Thoracic Aortic Aneurysm Endovascular Graft uses a delivery system that is commercially available from Cook Inc., Bloomington, Ind., and may be suitable for delivering and deploying an aortic prosthesis in accordance with the present embodiments.

A method of deploying a prosthesis with a body lumen of a patient with any of the disclosed delivery systems or components for treatment of diseases of the body lumen, such as for example, aortic dissection and aortic aneurysm in an aorta will be described. A proximal end of a delivery system in its delivery configuration loaded with a prosthesis in its radially compressed configuration, such as shown in FIG. 1, is inserted into a body lumen, using for example, various approaches, and the catheter body traverses through the lumen to a treatment site. Delivering of any one of the disclosed prostheses may include femoral delivery, brachial delivery, axillary delivery, subclavian delivery, and/or transapical delivery. Prior to insertion, a guide wire may be advanced to the treatment site so the delivery system may track along it to the treatment site. The operator may use visual indication techniques such as fluoroscopy to aid in the movement of the system through the body lumen.

Once the loaded prosthesis is placed at the desired site of treatment, the outer sheath is removed from the loaded prosthesis to allow for radial expansion to the deployed configuration, such as shown in FIG. 6. Removal or distal retraction of the other sheath may be accomplished distal retraction of the pull members. For example, the operator may grab the pull member extending out of sheath hub with hands or a tool, such as pliers, and apply the retraction force manually. For example, a portion of the pull member may be wound around a spool portion of the handle of the delivery system, such as shown in FIG. 4. This may be achieved by rotating an actuator coupled to the handle. When the rotatable actuator has a ratcheted configuration, the pull member(s) may be locked into a fixed positon to further structurally support the axially collapsible segment in its extended configuration, such as shown in FIG. 2 and FIG. 5A. With ratcheting, the winding may be urged to occur in a first single direction to aid the operator in the direction for retraction and to inhibit inadvertent movement of the outer sheath in the proximal direction. When distal retraction of the pull member occurs, the axially collapsible segment of the outer sheath is collapsed to a shorter length, such as shown in FIG. 5B, and the other sheath distally moves relative to the sheath hub held into a fixed position. In one example, the prosthesis may be deployed without retracting the sheath hub that is coupled to the outer sheath. The actuator may have an enlarged diameter in order to increase the mechanical advantage and reduce the effort required for retracting the outer sheath. The actuator may also be configured to receive a tool such as a socket or bar to aid in the effort for retraction. Once the prosthesis is delivered, the system may be removed from the body lumen. The system may be maintained in the body lumen and the inner cannula may be removed such that the outer sheath functions like an introducer sheath for allowing auxiliary devices to pass through. In another example, auxiliary devices may be inserted within the angled side ports and pushed along the outer sheath and body lumen to the treatment site. Collapsing the axially collapsible segment instead of retracting the outer sheath may provide the benefit of shortening the portion of the delivery system outside of the patient's body. The length savings may be due to the lack of retraction length for the outer sheath, and potentially the lack of sheath hub retraction.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A prosthesis delivery system, comprising:
   a handle;
   an inner cannula extending proximally from the handle;
   an outer sheath extending proximally from the handle, the outer sheath coaxially disposed over the inner cannula, the outer sheath including an axially collapsible segment and a non-collapsible body disposed proximal to the axially collapsible segment; and
   a pull member coupled between the handle and the axially collapsible segment or the non-collapsible body of the outer sheath, wherein the handle is operable to retract and wind the pull member such that the axially collapsible segment is collapsed,
   wherein a longitudinal length of the handle is shorter than a longitudinal length of the axially collapsible segment in an extension configuration prior to distal retraction of the pull member,
   wherein the longitudinal length of the handle is measured between a proximal end of a sheath hub and a distal end cap.

2. The prosthesis delivery system of claim 1, wherein the handle includes a spool portion, wherein the pull member is in a wound configuration about the spool portion during retraction of the pull member.

3. The prosthesis delivery system of claim 2, wherein the handle includes a rotatable actuator operable to place the pull member in the wound configuration.

4. The prosthesis delivery system of claim 1, wherein the pull member is disposed internally in an annular space defined between the outer sheath and the inner cannula, and the axially collapsible segment is movable between an extension configuration and a collapsed configuration, the axially collapsible segment in the extension position includes a profile that is sized no larger than a profile of the non-collapsible body.

5. The prosthesis delivery system of claim 1, wherein the sheath hub includes a central barrel, the central barrel including a pull member opening formed in a sidewall of the central barrel, the pull member opening sized to receive a cross-sectional area of the pull member.

6. The prosthesis delivery system of claim 5, wherein the handle includes a ratcheted rotatable annular actuator disposed about the central barrel, a segment of the central barrel defining a spool, wherein the ratcheted rotatable annular actuator is in coaxial relationship with the spool, and a distal end of the pull wire is coupled to the ratcheted rotatable annular actuator.

7. The prosthesis delivery system of claim 1, wherein the sheath hub includes one more angled side ports.

8. The prosthesis delivery system of claim 1, wherein the outer sheath includes one or more bonding ports, wherein the pull member is coupled to the outer sheath and an adhesive at least partially fills the one or more bonding ports for attachment to the pull member.

9. The prosthesis delivery system of claim 1, wherein the pull member comprises a protrusion coupled to the outer sheath.

10. The prosthesis delivery system of claim 1, wherein the pull member comprises an apertured portion coupled to the outer sheath.

11. The prosthesis delivery system of claim 1, wherein a wall of the outer sheath includes a reinforcing member, and the pull member is integrally formed from the reinforcing member.

12. The prosthesis delivery system of claim 1, wherein the pull member is a first pull member, the system comprising a second pull member coupled between the handle and the axially collapsible segment or the non-collapsible body of the outer sheath, the second pull member and the first pull member form a bend that is bonded with a wall of the outer sheath.

13. The prosthesis delivery system of claim 1, wherein the longitudinally collapsible segment comprises a woven structure.

14. The prosthesis delivery system of claim 1, wherein the longitudinally collapsible segment comprises a reduced wall segment.

15. The prosthesis delivery system of claim 1, wherein the axially collapsible segment comprises a helical member.

16. The prosthesis delivery system of claim 1, wherein the outer sheath includes reinforcing rings coupled to a proximal end of the pull member.

17. A method of deploying a prosthesis within a body lumen of a patient, the method comprising:
    introducing a proximal end of a delivery system into a body lumen to a treatment site, the delivery system including a handle, an outer sheath extending proximally from the handle, the outer sheath including an axially collapsible segment, and a pull member coupled between the handle and a portion of the outer sheath, wherein a prosthesis is disposed along a prosthesis retention region defined by the outer sheath and an inner cannula; and
    removing the outer sheath from the prosthesis at the treatment site by winding a portion of the pull member around a spool portion of the handle such that the axially collapsible segment of the outer sheath is at least partially collapsed and the prosthesis is capable of radial expansion to a deployed configuration,
    wherein a longitudinal length of the handle is shorter than a longitudinal length of the axially collapsible segment in an extension configuration prior to distal retraction of the pull member,
    wherein the longitudinal length of the handle is measured between a proximal end of a sheath hub and a distal end cap.

18. The method of claim 17, wherein the handle includes a rotatable actuator operable for winding the portion of the pull member.

19. A prosthesis delivery system, comprising:
    a sheath hub having a central barrel, wherein a segment of the central barrel defines a spool portion, and a rotatable actuator coaxially disposed about the central barrel and distal to the spool portion;
    an inner cannula extending proximally from the sheath hub, the inner cannula at least partially disposed within a central bore defined by the sheath hub;

an outer sheath extending proximally from the sheath hub, the outer sheath coaxially disposed over the inner cannula, the outer sheath including an axially collapsible segment; and a pull member coupled between a portion of the outer sheath and the rotatable actuator, the pull member extending through a pull member opening defined by the central barrel, wherein, in response to rotating the rotatable actuator in a first direction, the pull member is wound around the spool, the proximal end of the pull member is positioned closer to the handle, and the axially collapsible segment is at least partially collapsed, wherein a longitudinal length of the handle is shorter than a longitudinal length of the axially collapsible segment in an extension configuration minus a longitudinal length of the axially collapsible segment in a collapsed configuration, wherein the longitudinal length of the handle is measured between a proximal end of the sheath hub and a distal end cap.

\* \* \* \* \*